United States Patent [19]

Uda et al.

[11] Patent Number: 5,486,508
[45] Date of Patent: Jan. 23, 1996

[54] CYCLODEXTRIN COMPOSITION

[75] Inventors: Yoshiaki Uda, Takarazuka; Yoko Nishida, Ibaraki; Yasuaki Ogawa, Ohyamazaki, all of Japan

[73] Assignee: TAKEDA Chemical Industries Ltd., Osaka, Japan

[21] Appl. No.: 236,699

[22] Filed: Apr. 28, 1994

Related U.S. Application Data

[63] Continuation of Ser. No. 901,501, Jun. 19, 1992, abandoned.

[30] Foreign Application Priority Data

Jun. 21, 1991 [JP] Japan ................................. 3-150507
Sep. 10, 1991 [JP] Japan ................................. 3-230489

[51] Int. Cl.$^6$ ..................... A61K 31/715; A61K 31/335; A61K 47/00
[52] U.S. Cl. ............... 514/58; 514/59; 514/475; 514/777; 514/778
[58] Field of Search ................ 514/58, 59, 777, 514/778, 475

[56] References Cited

U.S. PATENT DOCUMENTS 5,024,998  6/1991  Bodor ........................ 514/58

FOREIGN PATENT DOCUMENTS

| 0149197 | 7/1985 | European Pat. Off. . |
|---|---|---|
| 0094157 | 7/1987 | European Pat. Off. . |
| 0325199A3 | 7/1989 | European Pat. Off. . |
| 0357061 | 8/1989 | European Pat. Off. . |
| 0335545 | 10/1989 | European Pat. Off. . |
| 0346006 | 12/1989 | European Pat. Off. . |
| 0354787 | 2/1990 | European Pat. Off. . |
| 0354767 | 2/1990 | European Pat. Off. . |
| 0359036 | 3/1990 | European Pat. Off. . |
| 0387650 | 3/1990 | European Pat. Off. . |
| 0371431 | 6/1990 | European Pat. Off. . |
| 0386667 | 9/1990 | European Pat. Off. . |
| 0399903 | 11/1990 | European Pat. Off. . |
| 0415294A2 | 3/1991 | European Pat. Off. . |
| 0461427 | 12/1991 | European Pat. Off. . |
| 5835968 | 9/1975 | Japan . |
| 62-281855 | 12/1987 | Japan . |
| 63-135402 | 6/1988 | Japan . |
| 63-251058 | 10/1988 | Japan . |

OTHER PUBLICATIONS

M. Kurozumi, et al., "Inclusion compounds of non–steroidal antiflammatory and other slightly soluble drugs with alpha and beta cyclodextrins in powdered form.", *Chemical and Pharmaceutical Bulletin*, vol. 23, 1975, pp. 3062–3068.

Uekama, K., "Pharmaceutical Applications of Cyclodextrin Complexations," *Yakugaku Zasshi* 101 (10) 857–873 (1981).

*Primary Examiner*—Marianne M. Cintins
*Assistant Examiner*—K. E. Weddington
*Attorney, Agent, or Firm*—David G. Conlin; George W. Neuner; Cara Z. Lowen

[57] ABSTRACT

A pharmaceutical composition comprising a slightly water-soluble drug, a cyclodextrin and a water-soluble organic solvent is disclosed. The composition improves water-solubility and stability of the slightly water-soluble drug. The pharmaceutical composition is particularly suitable for injection preparations.

11 Claims, No Drawings

CYCLODEXTRIN COMPOSITION

This is a continuation of application Ser. No. 07/901,501 filed on Jun. 19, 1992; now abandoned.

FIELD OF THE INVENTION

The present invention relates to a cyclodextrin composition and the production thereof. More specifically, in the present invention, a complex of a slightly water-soluble drug dissolved in a water-soluble organic solvent with a cyclodextrin is formed to improve the water-solubility and stability of the slightly water-soluble drug. The complex is useful for pharmaceutical compositions, particularly, injection preparations.

BACKGROUND OF THE INVENTION

As the conventional methods for forming a complex or inclusion compound of a slightly water-soluble drug with a cyclodextrin, there are a method wherein a saturated aqueous solution of a drug and a cyclodextrin are cooled and the resulting complex is precipitated, a method wherein an aqueous solution of a drug and a cyclodextrin is lyophilized [M. Kurozumi et al., Chem. Pharm. Bull., 23, 1421 (1975)], a mixing and pulverizing method [Y. Nakai et al., Chem. Pharm. Bull., 26, 2419 (1978)] and the like. However, the complexes of a slightly water-soluble drug with a cyclodextrin obtained by these methods do not have so high water-solubility and their water-solubility is insufficient for injection preparations. Further, in the complexes, the stability of drugs are sometimes deteriorated.

OBJECTS OF THE INVENTION

The main object of the present invention is to develop a composition applicable to injection preparations by improving the water-solubility of a slightly water-soluble drug and further improving the stability of the drug.

This object as well as other objects and advantages of the present invention will become apparent to those skilled in the art from the following description.

SUMMARY OF THE INVENTION

The present inventors have studied intensively to improve the water-solubility of slightly water-soluble drugs. As a result, the following has been found.

A slightly water-soluble drug is dissolved in a water-soluble organic solvent. On the other hand, a cyclodextrin is dissolved in water. When the latter aqueous cyclodextrin solution is gradually added to the former solution of the water-soluble organic solvent, the resulting mixture sometimes becomes cloudy upon addition of the aqueous solution. However, when the aqueous solution is further added, the mixture becomes clear. A powdered composition can be obtained by evaporating and distilling off the water-soluble organic solvent and water from the mixture. In many cases, the composition thus obtained forms an inclusion compound with the cyclodextrin. The composition has a very high water-solubility, which is 3 to 50 times higher than that of compositions obtained by the conventional techniques. Further, the composition has a high solution velocity and, when a specific cyclodextrin is selected, an unstable drug can be stabilized. Thus, the present invention has been completed.

That is, the present invention provides a pharmaceutical composition comprising a slightly water-soluble drug, a cyclodextrin and a water-soluble organic solvent. The composition of the invention may be in the form of a powdered pharmaceutical composition comprising a slightly water-soluble drug, a cyclodextrin and 0.1 to 10% by weight, preferably 0.1 to 3% by weight of a water-soluble organic solvent. Further, the present invention provides a process for producing a powdered complex of a slightly water-soluble drug with a cyclodextrin which comprises dissolving a slightly water-soluble drug in a water-soluble organic solvent and mixing the resulting solution with an aqueous solution of the cyclodextrin and, optionally, removing the water-soluble organic solvent and water. The pharmaceutical composition or the complex of the present invention is applicable to injection preparations.

DETAILED DESCRIPTION OF THE INVENTION

The slightly water-soluble drug to be used in the present invention is a drug whose solubility in water or a buffer is 1% (w/v) or lower, and the slightly water-soluble drug may be a salt thereof which is generally used in pharmaceutical compositions. Further, it is desirable that the drug has the solubility of 1% (w/v) or higher in the water-soluble organic solvent. Examples of the drug include anti-inflammatory agents, analgesics, tranquilizers, sedatives, antineoplastic agents, antifungal agents, antibiotics, antilipemic agents and the like. In particular, fumagillol derivatives having angiogenesis inhibitory activity are suitable for use as an antineoplastic agent in the present invention. Examples of the fumagillol derivative include a fumagillin derivative of the general formula:

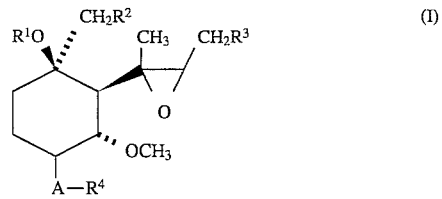

wherein $R^1$ is hydrogen; $R^2$ is halogen, $N(O)mR^5R^6$, $N^+R^5R^6R^7 \cdot X^-$, $S(O)nR^5$ or $S^+R^5R^6 \cdot X^-$ (wherein $R^5$, $R^6$ and $R^7$ are independently an optionally substituted hydrocarbon or heterocyclic group; $X^-$ is a counter anion; m is 0 or 1; n is an integer of 0 to 2; and $R^5$ and $R^6$ together with the adjacent nitrogen or sulfur atom may form an optionally substituted nitrogen- or sulfur-containing heterocyclic group which may form a condensed ring); or $R^1$ and $R^2$ together represent a bond; $R^3$ is 2-methyl-1-propenyl group or isobutyl group; A is O or $NR^8$ (wherein $R^8$ is hydrogen or an optionally substituted lower alkyl or aryl group); and $R^4$ is hydrogen, an optionally substituted hydrocarbon group or an optionally substituted acyl group; or a salt thereof and the like.

In the above general formula (I), halogen represented by $R^2$ includes fluorine, chlorine, bromine and iodine. When $R^1$ and $R^2$ together represent a bond, an epoxy ring is formed.

The hydrocarbon group of the optionally substituted hydrocarbon group represented by $R^5$, $R^6$ and $R^7$ includes a straight or branched chain $C_{1-6}$ alkyl (e.g., methyl, ethyl, propyl, isopropyl, butyl, isobutyl, sec-butyl, pentyl, isopentyl, hexyl, etc.), $C_{2-6}$ alkenyl (e.g., vinyl, allyl, 2-butenyl, methylallyl, 3-butenyl, 2-pentenyl, 4-pentenyl, 5-hexenyl, etc.), $C_{2-6}$ alkynyl e.g., ethynyl, propargyl, 2-butyn-1-yl, 3-butyn-1-yl, 1-pentyn-3-yl, 3-pentyn-1-yl, 4-pentyn-2-yl, 3-hexyn-1-yl, etc.), $C_{3-6}$ cycloalkyl (e.g., cyclopropyl, cyclobutyl, cyclopentyl, cyclohexyl, etc.), $C_{3-6}$ cycloalkenyl (e.g., cyclobutenyl, cyclopentenyl, cyclohexenyl, cyclohexadienyl, etc.), $C_{7-13}$ aralkyl (e.g., benzyl, 1-phenethyl, 2-phenethyl, etc.), and $C_{6-10}$ aryl (e.g., phenyl, naphthyl, etc.).

The heterocyclic group of the optionally substituted heterocyclic group represented by $R^5$, $R^6$ and $R^7$ includes a 5-or 6-membered heterocyclic group containing 1 to 4 hetero atoms (e.g., nitrogen, oxygen, sulfur, etc.), for example, 2-furyl, 2-thienyl, 4-thiazolyl, 4-imidazolyl, 4-pyridyl, 1,3, 4-thiadiazol-2-yl, tetrazolyl or the like. Further, the heterocyclic group may be condensed with a 5- or 6-membered ring which may include one to three hetero atoms such as N, O and S other than carbon atoms (e.g., benzene, pyridine, cyclohexane, etc.) to form a bicyclic group (e.g., 8-quinolyl, 8-purinyl, etc.).

The nitrogen-containing heterocyclic group which may be formed by $R^5$ and $R^6$ together with the adjacent nitrogen atom includes a 4- to 7-membered nitrogen-containing heterocyclic group which may include one to three hetero atoms such as N, O and S other than a nitrogen atom (e.g., pyrrolidin-1-yl, piperazino, morpholino, piperazin-1-yl, etc.).

The sulfur-containing heterocyclic group which may be formed by $R^5$ and $R^6$ together with the adjacent sulfur atom includes a 4- to 7-membered sulfur-containing heterocyclic group which may include one to three hetero atoms such as N, O and S other than a sulfur atom (e.g., tetrahydrothiophen-1-yl, 1,4-thioxan-1-yl, etc.).

The nitrogen- or sulfur-containing heterocyclic group which may be formed by $R^5$ and $R^6$ together with the adjacent nitrogen or sulfur atom may be condensed with a 5- or 6-membered ring (e.g., benzene, pyridine, pyrazine, pyridazine, cyclohexane, etc.) to form a bicyclic group (e.g., isoindolin-2-yl, 2-isoquinolyl, 1,3-dihydrobenzo[c] thiophen-2-yl, 2,3-dihydrobenzo[b]thiophen-1-yl, 3,4-dihydro-1H-2-benzopyran-2-yl, 3,4-dihydro-2H-1-benzopyran-1-yl, 1,2,4,5-tetrahydro-3-benzothiepin-3-yl, 1,3-dihydrothieno[3,4-c]pyridin-2-yl, 5,7-dihydrothieno[3,4-b]pyrazin-6-yl, 5,7-dihydrothieno[3,4-d]pyridazin-6-yl, etc.).

The lower alkyl group of the optionally substituted lower alkyl group represented by $R^8$ includes a $C_{6-10}$ alkyl group (e.g., methyl, ethyl, propyl, isopropyl, butyl, isobutyl, secbutyl, pentyl, isopentyl, hexyl, etc.).

The aryl group of the optionally substituted aryl group represented by $R^8$ includes a $C_{6-10}$ aryl group (e.g., phenyl, naphthyl, etc.).

The hydrocarbon group of the optionally substituted hydrocarbon group represented by $R^4$ includes those described above with respect to that of the optionally substituted hydrocarbon represented by $R^5$, $R^6$ $R^7$.

When the hydrocarbon group represented by $R^4$ is an alkenyl group, preferably, it has no substituent.

The optionally substituted acyl group represented by $R^4$ includes residues of optionally substituted acids such as carboxylic acid acyl, sulfonic acid acyl, carbamoyl, thiocarbamoyl and sulfamoyl which may have a substituent or substituents (wherein an acyl group derived from the corresponding acid). For example, they are alkanoyl, aroyl, heterocyclic carbonyl, carbamoyl, thiocarbamoyl, arylsulfonyl, alkylsulfonyl, sulfamoyl, alkoxycarbonyl, aryloxycarbonyl and the like each of which may have one or more substituents.

The alkanoyl group of the above optionally substituted alkanoyl group includes a $C_{1-6}$ alkanoyl group (e.g., formyl, acetyl, propionyl, isopropionyl, butyryl, pentanoyl, hexanoyl, etc.).

The aroyl group of the optionally substituted aroyl group includes a $C_{7-11}$ aroyl group (e.g., benzoyl, 1-naphthoyl, 2-naphthoyl, etc.).

The heterocyclic carbonyl group of the optionally substituted heterocyclic carbonyl group includes a 5- or 6-membered heterocyclic carbonyl group containing 1 to 4 hetero atoms (e.g., nitrogen, oxygen, sulfur, etc.), for example, 2-furoyl, 2-thenoyl, nicotinyl, isonicotinyl and the like.

The arylsulfonyl group of the optionally substituted arylsulfonyl group includes a $C_{6-10}$ arylsulfonyl group (e.g., benzenesulfonyl, 1-naphthylsulfonyl, 2-naphthylsulfonyl, etc.).

The alkylsulfonyl group of the optionally substituted alkylsulfonyl group includes a $C_{1-6}$ alkylsulfonyl group (e.g., methylsulfonyl, ethylsulfonyl, etc.).

The alkoxycarbonyl group of the optionally substituted alkoxycarbonyl group includes a $C_{2-7}$ alkoxycarbonyl group (e.g., methoxycarbonyl, ethoxycarbonyl, isobutoxycarbonyl, etc.).

The aryloxycarbonyl group of the optionally substituted aryloxycarbonyl group includes a $C_{7-11}$ aryloxycarbonyl group (e.g., phenoxycarbonyl, 1-naphthyloxycarbonyl, 2-naphthyloxycarbonyl, etc.).

The optionally substituted hydrocarbon or heterocyclic group represented by $R^5$, $R^6$ and $R^7$; the optionally substituted nitrogen- or sulfur-containing heterocyclic group formed by $R^5$ and $R^6$ together with the adjacent nitrogen or sulfur atom which may be condensed with a further ring; the optionally substituted lower alkyl or aryl group represented by $R^8$; as well as the optionally substituted hydrocarbon group and the optionally substituted acyl group (alkanoyl, aroyl, heterocyclic carbonyl, carbamoyl, thiocarbamoyl, arylsulfonyl, alkylsulfonyl, sulfamoyl, alkoxycarbonyl or aryloxycarbonyl) represented by $R^4$ may contain 1 to 3 substituents at the possible positions.

Such substituents includes, for example, a $C_{1-6}$ alkyl group (e.g., methyl, ethyl, propyl, isopropyl, butyl, isobutyl, sec-butyl, pentyl, isopentyl, hexyl, etc.), a $C_{2-6}$ alkenyl group (e.g., vinyl, allyl, 2-butenyl, methylallyl, 3-butenyl, 2-pentenyl, 4-pentenyl, 5-hexenyl, etc.), a $C_{2-6}$ alkynyl group (e.g., ethynyl, propargyl, 2-butyn-1-yl, 3-butyn-2-yl, 1-pentyn-3-yl, 3-pentyn-1-yl, -4-pentyn-2-yl, 3-hexyn-1-yl, etc.), a $C_{3-6}$ cycloalkyl group (e.g., cyclopropyl, cyclobutyl, cyclopentyl, cyclohexyl, etc.), a $C_{3-6}$ cycloalkenyl group (e.g., cyclobutenyl, cyclopentenyl, cyclohexenyl, cyclohexadienyl, etc.), a $C_{6-10}$ aryl group (e.g., phenyl, naphthyl, etc.), amino, a mono-$C_{1-6}$ alkylamino group (e.g., methylamino, ethylamino, isopropylamino, etc.), a di-$C_{1-6}$ alkylamino group (e.g., dimethylamino, diethylamino, etc.), azido, nitro, a halogen (e.g., fluorine, chlorine, bromine, iodine, etc.), hydroxyl, a $C_{1-4}$ alkoxy group (e.g., methoxy, ethoxy, etc.), a $C_{6-10}$ aryloxy group (e.g., phenoxy, naphthyloxy, etc.), a $C_{1-6}$ alkylthio group (e.g., methylthio, ethylthio, propylthio, etc.), a $C_{6-10}$ arylthio group (e.g., phenylthio, naphthylthio, etc.), cyano, carbamoyl, carboxyl, a $C_{1-4}$ alkoxycarbonyl group (e.g., methoxycarbonyl, ethoxycarbonyl, etc.), a $C_{7-11}$ aryloxycarbonyl group (e.g., phenoxycarbonyl, 1-naphthyloxycarbonyl, 2-naphthyloxycarbonyl, etc.), a carboxy-$C_{1-4}$ alkoxy group (e.g., carboxymethoxy, 2-carboxyethoxy, etc.), a $C_{1-6}$ alkanoyl group (e.g., formyl, acetyl, propionyl, isopropionyl, butyryl, pentanoyl, hexanoyl, etc.), a $C_{7-11}$ aroyl group (e.g., benzoyl, 1-naphthoyl, 2-naphthoyl, etc.), a $C_{6-10}$ arylsulfonyl group (e.g., benzenesulfonyl, 1-naphthylsulfonyl, 2-naphthylsulfonyl, etc.), a $C_{1-6}$ alkylsulfinyl group (e.g., methylsulfinyl, ethylsulfinyl, etc.), a $C_{6-10}$ arylsulfinyl group (e.g., benzenesulfinyl, 1-naphthylsulfinyl, 2-naphthylsulfinyl, etc.), a $C_{1-6}$ alkylsulfonyl group (e.g., methylsulfonyl, ethylsulfonyl, etc.), a 5- or 6-membered heterocyclic group containing 1 to 4 hetero atoms (e.g., nitrogen, oxygen, sulfur, etc.) (e.g., 2-furyl, 2-thienyl, 4-thiazolyl, 4-imidazolyl, 4-pyridyl, 1,3, 4-thiadiazol-2-yl, 1-methyl-5-tetrazolyl, etc.), a 5- or 6-membered heterocyclic carbonyl group containing 1 to 4 hetero atom (e.g., nitrogen, oxygen, sulfur, etc.) (e.g., 2-furoyl, 2-thenoyl, nicotinoyl, isonicotinoyl, etc.), a 5- or 6-membered heterocyclic thio group containing 1 to 4 hetero atoms (e.g., nitrogen, oxygen, sulfur, etc.) (e.g., 4-pyridylthio, 2-pyrimidylthio, 1,3,4-thiadiazol-2-ylthio, 1-methyl-5-tetrazolylthio, etc.) and the like. Further, the heterocyclic thio group may be condensed with benzene ring to form a condensed bicyclic thio group (e.g., 2-benzothiazolylthio, 8-quinolylthio, etc.). Furthermore, when $R^4$ represents a disubstituted carbamoyl, thiocabamoyl or sulfamoyl group, the substituents together with the nitrogen atom of the carbamoyl, thiocarbamoyl or sulfamoyl group may form a nitrogen-containing heterocyclic group (e.g., 4- to 7-membered nitrogen-containing heterocyclic group which may include one to three hetero atoms (e.g., N, O, S, etc.) other than a nitrogen atom, such as pyrrolidin-1-yl, piperidino, morpholino, piperazin-1-yl, 4-methylpiperazin-1-yl, 4-phenylpiperazin-1-yl, etc.).

The substituent in the optionally substituted hydrocarbon or heterocyclic group represented by $R^5$, $R^6$ and $R^7$; the substituent in the optionally substituted nitrogen- or sulfur-containing heterocyclic group which may be formed by $R^5$ and $R^6$ together with the adjacent nitrogen or sulfur atom and may be condensed with a further ring; the substituent in the optionally substituted lower alkyl group or aryl group represented by $R^8$; as well as the substituent in the optionally substituted hydrocarbon group and optionally substituted acyl group (alkanoyl, aroyl, heterocyclic carbonyl, carbamoyl, thiocarbamoyl, arylsulfonyl, alkylsulfonyl, sulfamoyl, alkoxycarbonyl or aryloxycarbonyl) represented by $R^4$ may further contain 1 to 3 substituents at the possible positions.

Examples of such substituents include the aforementioned $C_{3-6}$ alkyl group, $C_{3-6}$ alkenyl group, $C_{2-6}$ alkynyl group, $C_{3-6}$ cycloalkyl group, $C_{3-6}$ cycloalkenyl group, $C_{6-10}$ aryl group, amino group, mono-$C_{1-6}$ alkylamino group, di-$C_{1-6}$ alkylamino group, azido, nitro, halogen, hydroxyl, $C_{1-4}$ alkoxy group, $C_{6-10}$ aryloxy group, $C_{1-6}$ alkylthio group, $C_{6-10}$ arylthio group, cyano, carbamoyl, carboxyl, $C_{1-4}$ alkoxycarbonyl group, $C_{7-11}$ aryloxycarbonyl group, carboxy-$C_{1-4}$ alkoxy group, $C_{1-6}$ alkanoyl group, $C_{7-11}$ aroyl group, $C_{6-10}$ arylsulfonyl group, $C_{1-6}$ alkylsulfinyl group, $C_{6-10}$ arylsulfinyl group, $C_{1-6}$ alkylsulfonyl group, 5- or 6-membered heterocyclic group, 5-or 6-membered heterocyclic carbonyl group and 5- or 6-membered heterocyclic thio group and the like.

The counter anion represented by $X^-$ includes, for example, halogen ion (e.g., iodide ion, bromide ion, chloride ion, etc.), sulfate ion, phosphate ion, nitrate ion, perchlorate ion, tetrafluoroborate ion, methanesulfate ion, p-tolylsulfate ion, benzenesulfate ion, hydroxyl ion, organic carboxylate ion (e.g., oxalate ion, maleate ion, fumarate ion, succinate ion, citrate ion, lactate ion, trifluoroacetate ion, lactobionate ion, acetate ion, propionate ion, tartrate ion, ethyl succinate ion, etc.) and the like.

The compound (I) has an asymmetric center in its molecule and is optically active. Its absolute configuration is based on the starting material, fumagillol. When the configuration is shown, the absolute configuration is the same as that of fumagillol. The mode of bonding of the substituents on the cyclohexane ring is as follows: ..., ▬▬▬ and ▬▬▬ represent α-bond, β-bond and either α- or β-bond, respectively.

When the compound (I) has an acidic substituent (e.g., carboxyl, etc.) or a basic substituent (e.g., amino, mono-lower alkylamino, di-lower alkylamino, nitrogen-containing heterocyclic group, etc.), it may be used as a physiologically acceptable salt thereof. Examples of the physiologically acceptable salt include those with inorganic bases, organic bases, inorganic acids, organic acids, basic or acidic amino acids and the like. As the inorganic base which can form these salts, there are, for example, alkali metal (e.g., sodium, potassium, etc.) and alkaline earth metal (e.g., calcium, magnesium, etc.) and the like; as the organic base, there are, for example, trimethylamine, triethylamine, pyridine, picoline, N,N-dibenzylethylenediamine, ethanolamine, diethanolamine, tris(hydroxymethyl)aminomethane, dicyclohexylamine and the like; as the inorganic acid, there are, for example, hydrochloric acid, hydrobromic acid, sulfuric acid, nitric acid, phosphoric acid and the like; as the organic acid, there are, for example, formic acid, acetic acid, trifluoroacetic acid, oxalic acid, tartaric acid, fumaric acid, maleic acid, methanesulfonic acid, benzenesulfonic acid, p-toluenesulfonic acid and the like; and as the basic or acidic amino acid, there are, for example, arginine, lysine, ornithine, aspartic acid, glutamic acid and the like. Among these salts, salts with bases (i.e., salts with inorganic bases, salts with organic bases, salts with basic amino acids) represent those formed with the carboxyl group in the substituent of the compound (I), and salts with acids (i.e., salts with inorganic acids, salts with organic acids, salts with acidic amino acids) represent those which can be formed with amino, mono-lower alkylamino group, di-lower alkylamino group, nitrogen-containing heterocyclic group or the like in the substituent of the compound (I).

When the compound (I) has a di-lower alkyl amino group, a nitrogen-containing heterocyclic group or a nitrogen-containing aromatic heterocyclic group, the nitrogen atom in these groups may be further alkylated to form a quaternary ammonium group (e.g., trimethylammonium, N-methylpyridinium, N-methylpyrrolidin-1-ylium, etc.), and the counter anion thereof includes those shown with respect to the aforementioned counter anion represented by $X^-$.

In the compound (I), preferably, $R^1$ and $R^2$ together represent a bond, or $R^1$ is hydrogen and $R^2$ is $N(O)mRsR^5R^6$, $N^+R^5R^6R^7 \cdot X^-$, $S(O)nR^5$ or $S^+R^5R^6 \cdot X^-$. Particularly, it is preferred that $R^2$ is $S^+R^5R^6 \cdot X^-$ wherein $R^5$ and $R^6$ are a hydrocarbon group and $X^-$ is a halogen.

A is preferably O or NH. $R^3$ is preferably 2-methyl-1-propenyl and $R^4$ is preferably a substituted carbamoyl or ureido.

The compound represented by the general formula (I) or a salt thereof can be produced by using, as a starting material, fumagillol [Tarbell, D. S. et al., J. Am. Chem. Soc., 83, 3096 (1961)] which is a hydrolyzate of fumagillin produced by a microorganism. The production process as well as physical and biological properties thereof are described in detail in EP-A 359,036, EP-A 357,061, EP-A 354,787 and the like. Preferred examples of the compound (I) include 6-O-(N-chloroacetylcarbamoyl)fumagillol,6α-(N'-chloroacetylureido)-6-desoxyfumagillol, 4-(N-chloroacetylcarbamoyloxy)-2-(1,2-epoxy-1,5-methyl-4-hexenyl)-1-(1,3-dihydrobenzo(c)thiophen-2-ylo)-3-methoxycyclohexanol chloride and the like.

Examples of the tranquilizer include diazepam, lorazepam, oxazepam and the like. Examples of the antifungal agent include griseofulvin, lankacidins [J. Antibiotics, 38, 877–885 (1985)], furukunazole and the like. Examples of the antibiotic include cefotiam hexetil and the like. Examples of the antilipemic agent include clofibrate, AL-294 [Chem. Pharm. Bull., 38, 2792–2796 (1990)] and the like. Other examples of the slightly water-soluble drug include piroxicam, diacerin, diltiazem, megestrol acetate, nifedipine, nicergoline, ketoprofen, naproxen, diclofenac, ibuprofen, prostaglandins and the like.

The cyclodextrin to be used in the present invention is a cyclic oligosaccharide composed of 6 to 12 glucose units wherein hydroxyl groups at 2-, 3- and 6-positions may be partly or totally substituted with other functional groups.

Examples of the cyclodextrin (hereinafter sometimes abbreviated to CyD) include a compound represented by the general formula:

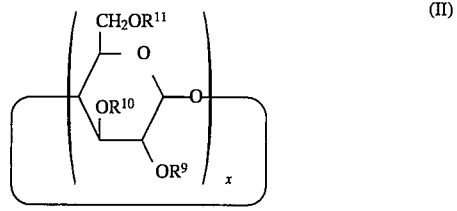
(II)

wherein X is an integer of 6 to 12; $R^9 R^{10}$ and $R^{11}$ in respective repetition units are the same or different and are independently hydrogen, an alkyl, a monohydroxyalkyl, a dihydroxyalkyl, a carboxyalkyl or a sugar residue. Specific examples thereof include α-CyD (x=6), β-CyD (x=7), γ-CyD (x=8), δ-CyD (x=9) and the like as well as their derivatives having etherified hydroxyl group.

As the alkyl group represented by $R^9$ to $R^{11}$, there are, for example, $C_{1-4}$ alkyl such as methyl, ethyl, propyl and the like; as monohydroxyalkyl, there are, for example, monohydroxy-$C_{1-4}$ alkyl such as hydroxymethyl, 2-hydroxyethyl, 2-hydroxypropyl; as the dihydroxyalkyl group, there are, for example, dihydroxy-$C_{1-4}$ alkyl such as dihydroxymethyl, 2,2-dihydroxyethyl, dihydroxypropyl and the like; as the carboxyalkyl group, there are, for example, carboxy-$C_{1-4}$ alkyl such as carbox.ymethyl, 2-carboxyethyl and the like; as the sugar residue, there are, for example, glucosyl, maltosyl, panosyl and the like.

These cyclodextrins may be used alone or in combination thereof. Among them, cyclodextrins having high water-solubility are preferably used. In particular, dihydroxypropyl derivatives and maltosyl derivatives are preferably used. The amount of the cyclodextrin to be used is preferably 1 to 5 times, more preferably 1.2 to 2.5 times, in molar ratios based on the slightly-water-soluble drug.

In the composition of the present invention, in general, the drug is more stable when it is in the solid form. Therefore, preferably, the coexisting water-soluble organic solvent and water are removed to obtain a powdered composition. Examples of the method for removing them include lyophilization, drying under reduced pressure, vaporization under ordinary pressure and the like. For stabilizing the drug, lyophilization and lyophilization under reduced pressure wherein the composition is dried after freezing are suitable.

As the water-soluble organic solvent to be used in the present invention, there can, for example, be used hydrophilic organic solvents having sufficient quality for injection preparations. The lower content of the water-soluble organic solvent in the powdered composition is more preferable. In the composition of the present invention, however, it is difficult to remove the solvent completely. Then, the solvent content in the composition is preferably not more than 10% by weight, more preferably in the range of 0.1 to 5% by weight, much more preferably 0.5 to 3% by weight. For injection preparations, ethyl alcohol is often used as the water-soluble organic solvent. The solvent is not always limited to ethyl alcohol. Any hydrophilic organic solvents can be used as long as the slightly water-soluble drug can be dissolved therein in a high concentration. As the water-soluble organic solvent, in addition to ethyl alcohol, there can be used, for example, other alcohols (e.g., methyl alcohol, isopropyl alcohol, etc.), ketones (e.g., acetone, etc.), nitriles (e.g., acetonitrile, etc.), sulfoxides (e.g., dimethyl sulfoxide, etc.), amides (e.g., dimethylformamide, etc.) and the like. Even when these solvents are used, the preparation can be used as injection preparations if the removal of the solvent is sufficient for application to injection preparations. Further, for administration other than injection, the composition can be used even if the removal of the solvent is insufficient.

In the production of the composition of the present invention, the slightly water-soluble drug is dissolved in the water-soluble organic solvent, especially ethyl alcohol, at about ordinary temperature (10° to 35° C.), if necessary, by warming to 60° C. The amount of the solvent to be used is usually 10 to 80 ml, preferably 20 to 40 ml per 1 g of the drug. On the other hand, the cyclodextrin is dissolved in water or a buffer solution. As the buffer solution, there are, for example, Walpole buffer solution, Menzel buffer solution, etc. The amount of water or buffer solution to be used is usually 1 to 50 ml, preferably 5 to 15 ml per 1 g of cyclodextrin. Normally, an aqueous solution of the cyclodextrin is gradually added with stirring to the above-prepared solution of the drug in the water-soluble organic solvent. Immediately after addition of the cyclodextrin solution, the entire mixture sometimes becomes cloudy. When the addition of the cyclodextrin solution is continued, the mixture becomes a clear solution. When the order of addition is reversed, sometimes, any clear solution cannot be obtained. The solution thus obtained is lyophilized or dried under reduced pressure to obtain a powder. In many cases, the powder obtained according to the above operations is the inclusion compound, or it forms a complex by electrostatic or hydrophobic interaction, hydrogen bond or the like. The powder may contain the slightly water-soluble drug and/or cyclodextrin other than the inclusion compound or the complex, and the composition of the present invention also include such a powder. For improving properties (filling properties into a vial, specific volume, destaticizing, etc.) of the powder thus obtained, conventional additives used in injection preparations such as sugars, preservatives, stabilizers and antistatic agents can be added. The powder obtained according to the above operations is readily soluble in distilled water for injection or an aqueous isotonic solution prepared from sodium chloride and sugars (glucose, mannitol, inositol, etc.). After dissolution, the slightly water-soluble drug can be administered as injection preparations intravenously, intramuscularly, subcutaneously or to focuses such as tumor or the like in an effective concentration for particular diseases.

Further, according to the conventional methods, the powder obtained by the present invention can be formed into pharmaceutical compositions other than injection preparations, for example, preparations for administering to the mucous membranes such as nasal, oral, rectal, vaginal mucous membranes, percutaneous preparations or implantation preparations.

The powder of the present invention is less toxic and manifests strong pharmacological activities, and is useful as a pharmaceutical composition for mammals (e.g., monkey, cattle, dog, human being, etc.).

The dosage of the powder of the present invention is varied depending upon a particular kind of drug, strength of the activity and the like. For treatment of an adult patient, normally, 1.0 mg to 5.0 g per day, preferably, 50 mg to 2.0 g per day of the powder of the present invention is administered by injection.

The following examples, comparative examples and experiments further illustrate the present invention in detail but are not to be construed to limit the scope thereof.

COMPARATIVE EXAMPLE 1

6-O-(N-chloroacetylcarbamoyl)fumagillol [hereinafter abbreviated as Compound A] (100 mg) was dissolved in ethyl alcohol (4 mg). Separately, maltosyl-β-cyclodextrin ($G_2\beta CD$) (726 mg)(Compound A:$G_2\beta CD$=1:2, molar ratio) was dissolved in water (15 ml). The aqueous solution was added to the above ethyl alcohol solution with stirring. The solution thus obtained was lyophilized to obtain a powder. Water (1 ml) was added to the powder (100 mg) to obtain a homogeneous solution of the present invention.

On the other hand, as an example of the conventional method, $G_2\beta CD$ (726 mg) was dissolved in water (10 ml), and Compound A (100 mg) was added and the mixture was stirred at 25° C. After 4 hours, the mixture was filtered through a filter having pore size of 0.22 μm.

The amounts of Compound A in the former homogeneous solution and the latter filtrate were determined by HPLC (high-performance liquid chromatography). Further, saturated solubility of mixed powder of Compound A and $G_2\beta CD$ in the same molar ratio at 25° C. and that of Compound A alone were determined by HPLC. As a result, solubility concentrations shown in Table 1 were obtained. As seen from Table 1, the result obtained by the conventional method is saturated solubility, while the result obtained by the present invention shows higher solubility concentration rather than the saturated solubility.

TABLE 1

| Comparison of solubilities | |
|---|---|
| Present invention | 42.0 mg/ml |
| Conventional method | 3.7 |
| Mixed powder of Compound A and $G_2\beta CD$ | 2.3 |
| Compound A alone | 1.7 |

REFERENCE EXAMPLE 2

Compound A (100 mg) was dissolved in ethyl alcohol (4 ml). Separately, 2-hydroxypropyl-β-cyclodextrin (2-HP-βCD)(686 mg)(Compound A:2-HP-βCD=1:2, molar ratio) was dissolved in water (15 ml). The aqueous solution was added to the above ethyl alcohol solution with stirring. The solution thus obtained was lyophilized to obtain a powder. Water (1 ml) was added to the powder (70 mg) to obtain a homogeneous solution of the present invention.

On the other hand, as an example of the conventional method, 2-HP-βCD (686 mg) was dissolved in water (10 ml). Compound A (100 mg) was added to the solution and the mixture was stirred at 25° C. After 4 hours, the mixture was filtered through a filter having pore size of 0.22 μm.

The amounts of Compound A in the former homogeneous solution and the latter filtrate were determined by HPLC. Further, saturated solubility of mixed powder of Compound A and 2-HP-βCD in the same molar ratio at 25° C. and that of Compound A alone were determined by HPLC. As a result, solubility concentrations shown in Table 2 were obtained. As seen from Table 2, the result obtained by the conventional method shows saturated solubility, while the result obtained by the present invention shows higher concentration solubility rather than the saturated solubility.

TABLE 2

| Comparison of solubilities | |
|---|---|
| Present invention | 35.2 mg/ml |
| Conventional method | 2.6 |
| Mixed powder of Compound A and 2-HP-βCD | 2.3 |
| Compound A alone | 1.7 |

Experiment 1

Stability of the powders of the present invention obtained in Comparative Examples 1 and 2 was compared with that of Compound A alone with maintaining them at 40° C. for 2 weeks. The residual amounts of Compound A was determined by HPLC. The results are shown in Table 3.

TABLE 3

| Stability | |
|---|---|
| | Residual rate |
| Mixed powder of Compound A and $G_2\beta CD$ | 100.6% |
| Mixed powder of Compound A and 2-HP-βCD | 39.0 |
| Compound A alone | 81.4 |

As seen from Table 2, solubility is improved depending upon by combinations of a particular kind of drug and a particular kind of cyclodextrin. However, stability is sometimes improved and sometimes lowered.

Experiment 2

According to the same manner as that described in Comparative Examples 1 and 2, various lyophilized powders were prepared with varying ratios of $G_2\beta CD$ or 2-HP-βCD to Compound A. Solubility of the powder thus obtained was determined. The results are shown in Table 4.

TABLE 4

| | Solubility | | |
|---|---|---|---|
| | Mixing molar ratio (Compound A:cyclodextrin) | | |
| | 1:1 | 1:1.5 | 1:2 |
| Compound A and $G_2\beta CD$ | 4.8 | 22.1 | 42.0 mg/ml |
| Compound A and 2-HP-βCD | 4.0 | 18.3 | 35.2 |

Experiment 3

According to the same manner as that described in Comparative Examples 1 and 2, various powders were prepared with varying mixing ratios. At this time, in the case of the molar ratio of 1:1.5, drying was carried out at 25° C. for 65 hours. In the case of the molar ratio of 1:2, drying was carried out at 25° C. for 42 hours and at 40° C. for 72 hours. The ethyl alcohol contents in each powder were determined by GLC (gas chromatography). The results are shown in Table 5.

TABLE 5

| | Ethyl alcohol contents | | |
|---|---|---|---|
| | Mixing molar ratio (Compound A:cyclodextrin) | | |
| | 1:1.5 (25° C.) | 1:2 (25° C.) | 1:2 (40° C.) |
| Compound A and G$_2$βCD | 1.3% | 1.4% | 1.5% |
| Compound A and 2-HP-βCD | 0.6% | 0.7% | — |

Experiment 4

Diazepam and clofibrate were selected as the slightly water-soluble drug, and a complex was prepared by using G$_2$βCD, according to the same manner as that described in Comparative Example 1. The solubility of the complex was compared with that of the drug alone. The results are shown in Table 6.

TABLE 6

| | Solubility | |
|---|---|---|
| Mixing molar ratio | solubility | |
| (Drug: G$_2$βCD) | Complex | Drug alone |
| Diazepam 1:10 | >4.0 mg/ml | 47 μg/ml |
| Clofibrate 1:10 | >4.3 | 36 |

EXAMPLE 1

Compound A (100 mg) was dissolved in ethyl alcohol (4 ml). Separately, β-cyclodextrin (βCD)(200 mg) was dissolved in water (15 ml). The aqueous solution was added to the above ethyl alcohol solution with stirring. The solution thus obtained was lyophilized to obtain the desired powder.

EXAMPLE 2

Compound A (100 mg) was dissolved in ethyl alcohol (4 ml). Separately of this solution, maltosyl-β-cyclodextrin (G$_2$DCD)(726 mg) was dissolved in water (15 ml). The aqueous solution was added to the above ethyl alcohol solution with stirring to obtain the desired composition.

EXAMPLE 3

Compound A (100 mg) was dissolved in ethyl alcohol (4 ml). Separately, dihydroxypropyl-β-cyclodextrin (DHP-βCD)(500 mg) was dissolved in water (15 ml). The aqueous solution was added to the above ethyl alcohol solution with stirring. The solution thus obtained was lyophilized to obtain the desired powder.

EXAMPLE 4

Cefotiam hexetil (100 mg) was dissolved in ethyl alcohol (4 ml). Separately, α-cyclodextrin (αCD)(200 mg) was dissolved in water (15 ml). The aqueous solution was added to the above ethyl alcohol solution with stirring. The solution thus obtained was lyophilized to obtain the desired powder.

EXAMPLE 5

Compound A (100 mg) was dissolved in acetone (4 ml). Separately, maltosyl-β-cyclodextrin (G$_2$βCD)(726 mg) was dissolved in water (15 ml). The aqueous solution was added to the above acetone solution with stirring. The solution thus obtained was lyophilized to obtain the desired powder.

EXAMPLE 6

Compound A (100 mg) was dissolved in acetonitrile (4 ml). Separately, maltosyl-β-cyclodextrin (G$_2$βCD)(726 mg) was dissolved in water (15 ml). The aqueous solution was added to the acetonitrile solution with stirring. The solution thus obtained was lyophilized to obtain the desired powder.

EXAMPLE 7

Compound A (100 mg) was dissolved in isopropyl alcohol (4 ml). Separately, maltosyl-β-cyclodextrin (G$_2$βCD)(726 mg) was dissolved in water (15 ml). The aqueous solution was added to the isopropyl alcohol solution with stirring. The solution thus obtained was lyophilized to obtain the desired powder.

EXAMPLE 8

Compound A (100 mg) was dissolved in ethyl alcohol (4 ml). Separately from this solution, glucosyl-β-cyclodextrin (G$_1$βCD) (645 mg) was dissolved in water (15 ml). The aqueous solution was added to the above ethyl alcohol solution with stirring to obtain the desired composition.

What is claimed is:

1. A powder composition which comprises a complex of a fumigillol derivative and a cyclodextrin prepared by: preparing a drug solution by dissolving in a water soluble organic solvent a slightly water soluble drug which is a fumagillol derivative represented by the formula:

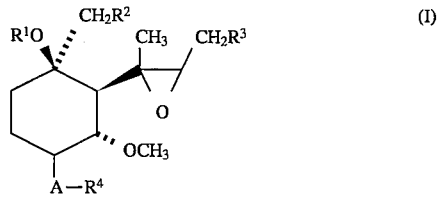

wherein $R^1$ is hydrogen; $R^2$ is halogen, $N(O)mR^5R^6$, $N^+R^5R^6R^7 \cdot X^-$, $S(O)nR^5$ or $S^+R^5R^6 \cdot X^-$, wherein $R^5$, $R^6$ and $R^7$ are independently an optionally substituted hydrocarbon or heterocyclic group; $X^-$ is a counter anion; m is 0 or 1; n is an integer of 0 to 2; or $R^5$ and $R^6$ together with the adjacent nitrogen or sulfur atom may form an optionally substituted nitrogen- or sulfur-containing heterocyclic group which may form a condensed ring; or $R^1$ and $R^2$ together represent a bond; $R^3$ is 2-methyl-1-propenyl group or isobutyl group; A is O or $NR^8$, wherein $R^8$ is hydrogen or an optionally substituted lower alkyl or aryl group; and $R^4$ is hydrogen, an optionally substituted hydrocarbon group or an optionally substituted acyl group; or a physiologically acceptable salt thereof, preparing a cyclodextrin solution by dissolving a cyclodextrin in water or an aqueous buffer;

mixing the cyclodextrin solution into the drug solution so that the resulting solution contains a molar ratio of the cyclodextrin to the drug of about 1.2:1 to 3:1 and the water soluble organic solvent is present in an amount from about 0.1 to 10% by weight based on the total solids; and lyophilizing or drying under reduced pressure the resulting mixed solution to form a powder;

wherein the powder has substantially increased solubility in aqueous solution compared to the drug.

2. A powder composition according to claim 1, wherein the amount of water soluble organic solvent is 0.1 to 3% by weight.

3. A powder composition according to claim 1, wherein $R^1$ is hydrogen and $R^2$ is $N(O)mR^5R^6$, $N^+R^5R^6R^7 \cdot X^-$, $S(O)nR^5$ or $S^+R^5R^6 \cdot X^-$ or $R^1$ and $R^2$ together represent a bond; $R^3$ is 2-methyl-1-propenyl group; A is O or NH; $R^4$ is a substituted carbamoyl or ureido.

4. A powder composition according to claim 1, wherein the fumagillol derivative is 6-O-(N-chloroacetyl-carbamoyl) fumagillol.

5. A powder composition according to claim 1, wherein the cyclodextrin is a compound of the formula:

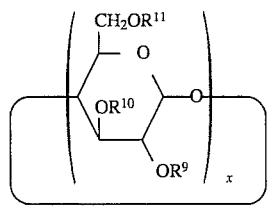

(II)

wherein x is an integer from 6 to 12, $R^9$, $R^{10}$ and $R^{11}$ in respective repetition units are the same or different and are independently hydrogen, an alkyl, a monohydroxyalkyl, a dihydroxyalkyl, a carboxyatkyl or a sugar residue.

6. A powder composition according to claim 5, wherein the cyclodextrin is a member selected from the group consisting of dihydoxypropyl-β-cyclodextrin and maltosyl-β-cyclodextrin.

7. A powder composition according to claim 1, wherein the cyclodextrin is maltosyl-β-cyclodextrin.

8. A powder composition according to claim 1, wherein the water-soluble organic solvent is a member selected from the group consisting of alcohols, ketones, nitriles, sulfoxides and amides.

9. A powder composition according to claim 1, wherein the water-soluble organic solvent is a member selected from the group consisting of methyl alcohol, ethyl alcohol, isopropyl alcohol, acetone, acetonitrile, dimethylsulfoxide and dimethylformamide.

10. A powder composition according to claim 1, wherein the water-soluble organic solvent is ethyl alcohol.

11. A powder composition according to claim 1 further comprising a carrier to provide an injection preparation.

* * * * *